United States Patent
Scherer et al.

(10) Patent No.: US 7,196,219 B2
(45) Date of Patent: Mar. 27, 2007

(54) PREPARATION OF ANILINEBORONIC ACIDS AND DERIVATIVES THEREOF

(75) Inventors: Stefan Scherer, Buettelborn (DE); Andreas Meudt, Hofhetn (DE); Bernd Lehnemann, Frankfurt (DE); Alexei Kalinin, Springfield, MO (US); Victor Snieckus, Kingston (CA)

(73) Assignee: Archimica GmbH, Frankfurt am Main (DE)

( * ) Notice: Subject to any disclaimer, the term of this patent is extended or adjusted under 35 U.S.C. 154(b) by 390 days.

(21) Appl. No.: 10/846,463

(22) Filed: May 14, 2004

(65) Prior Publication Data
US 2005/0038287 A1 Feb. 17, 2005

(30) Foreign Application Priority Data
May 19, 2003 (DE) .................... 103 22 843

(51) Int. Cl.
C07F 5/02 (2006.01)
C07F 5/04 (2006.01)

(52) U.S. Cl. .......................... 564/8; 568/6
(58) Field of Classification Search ............. None
See application file for complete search history.

(56) References Cited

U.S. PATENT DOCUMENTS

| | | | |
|---|---|---|---|
| 3,133,951 A | 5/1964 | Nutzel | |
| 3,206,446 A | 9/1965 | Hillman | |
| 4,978,794 A | 12/1990 | Brown | |
| 6,461,388 B1 | 10/2002 | Chassot et al. | |

OTHER PUBLICATIONS

Database CAPLUS on STN, Acc. No. 1959:16987, Gilman et al., Journal of the American Chemical Society (1958), 80, p. 3609-3611 (abstract).*
The Merck Index 12th ed. (1996). BUDAVARI editor., Merck & Co, Inc., Whitehouse Station, NJ, p. ONR-89.*
Miyaura et al., Tetrahedron Letters (1979), 36, p. 3437-3440.*
Database CAPLUS on STN, Acc. No. 2002:576150, Klis et al., Main Group Metal Chemistry (2002), 25(8), p. 479-484 (abstract).*
Database CASREACT on STN, No. 137:353082, Klis et al., Main Group Metal Chemistry (2002), 25(8), p. 479-484 (abstract).*
Baudoin, O. et al., "Palladium-Catalized Borylation of Ortho-substituted Phenyl Halides and Application to One-Pot synthesis of 2,2'Disubstituted Biphenyls", J. Org. Chem., No. 65, 2000, pp. 9268-9271.
Kotha S. et al., "Recent Applications of the Suzuki-Miyaura Cross-coupling Reaction in Organic Synthesis", TETRAHEDRON, Elsevier Sci Pub, Amsterdam, NL, Bd. 58, No. 48, Nov. 25, 2002, pp. 9633-9695.
Bezmenov, A., et al., "Hydroboration of isoprene and cis and trans-peperylenes", N.D. Zelinskii Institute of Organic Chemistry, Academy of Sciences, USSR, No. 12, pp. 2111-2120, Dec. 1965.
Mikhailove, B.M., et al., "Cyclic boron compounds formed during hydroboration of 1,3-butadiene", N. D. Zelinskii Institute of Organic Chemistry, Academy of Sciences, USSR, vol. 155, No. 1, pp. 141-144, Mar. 1964.
Mikhailove, B.M., et al., "Organoboron compounds CCXCV. Permanent allyl rearrangement in tris(3-methyl-2-buten-1-yl)borane and 1-allyl-2-(3-buten-1-yl)-4,4-dimethyl-5-chloromethyleneboracyclopentane", Zhurnal Obshchei Khimii (1975), 45(1), pp. 51-56, USSR.

* cited by examiner

*Primary Examiner*—Brian Davis
(74) *Attorney, Agent, or Firm*—ProPat, L.L.C.

(57) ABSTRACT

A process for preparing anilineboronic acid derivative of the formula I,

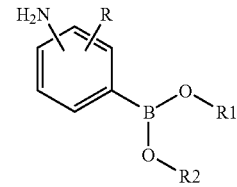

by converting an aniline to a diprotected aniline by introducing two protecting groups, metalating the diprotected aniline with a metalating agent and simultaneously or subsequently reacting with a boronic ester $B(OR^{1,2,3})_3$ to form a protected anilineboronic ester, which is converted, by detaching the protecting groups, to the anilineboronic esters of the formula (I).

26 Claims, No Drawings

PREPARATION OF ANILINEBORONIC ACIDS AND DERIVATIVES THEREOF

The invention relates to a process for preparing anilineboronic acids and their esters and salts, by protecting an optionally substituted aniline derivative on the nitrogen by exchanging all hydrogen atoms for one or more protecting groups and then metalating and then reacting with a suitable boron compound, to obtain, depending on the workup and removal of the protecting groups, the corresponding boronic acid, its anhydride or a boronic ester (EQUATION 1).

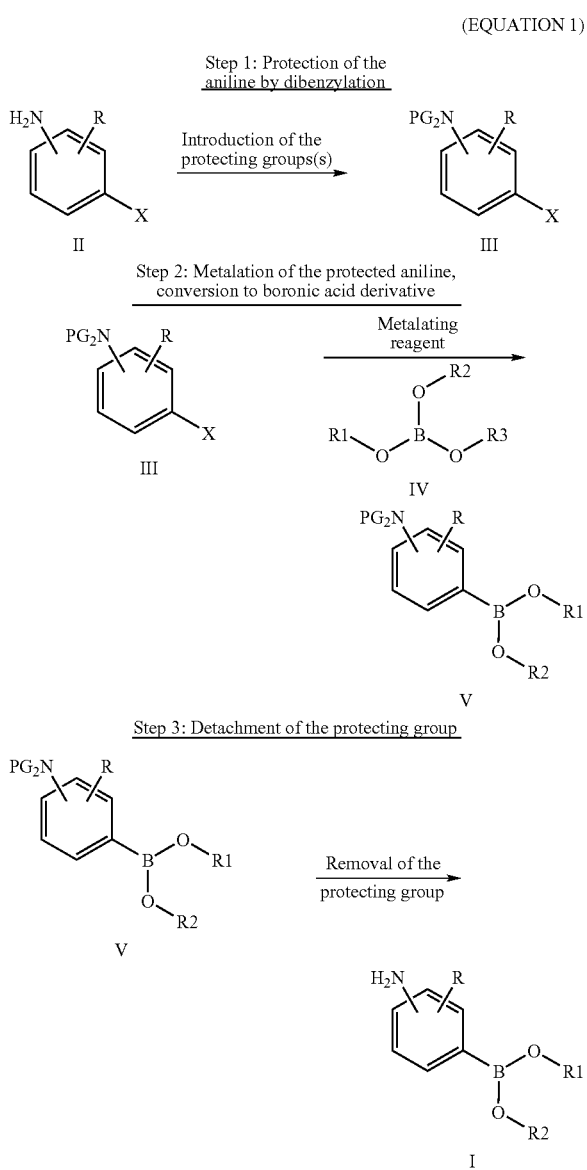

The application of transition metal-catalyzed reactions, especially for forming carbon-carbon bonds using palladium or nickel catalysts, has increasingly found use in the industrial synthesis of active pharmaceutical ingredients, specialty and fine chemicals, which frequently proceed under very mild conditions and with good chemoselectivities. An alkenyl halide, alkynyl halide, aryl halide or heteroaryl halide is generally coupled with an alkene (Heck reaction) or an organometallic compound. Especially asymmetrically substituted biphenyl derivatives which are not accessible by classical synthetic methods are prepared in this way. The most frequently applied method is the Suzuki or Suzuki-Miyaura coupling in which the boronic acids or their derivatives, occasionally also alkylboranes, are used as organometallic coupling partners. As a consequence of their comparatively low reactivity, these boron compounds tolerate the presence of many functional groups in the molecule and can even be converted in aqueous reaction media. Their toxicity is likewise low compared to other metal organyls of comparable reactivity, for example organotin compounds (Stille coupling).

Organic arylboronic acids and their derivatives are usually prepared by reacting an aryllithium or -magnesium compound with a trialkyl borate and subsequent aqueous-acidic hydrolysis.

This synthetic route cannot be applied directly to anilineboronic acids, since the two relatively acidic hydrogen atoms of the amino group make the preparation of an organometallic compound of the aniline impossible. Simple protection of the amino group, as is customary in peptide synthesis, is inadequate, since the second hydrogen atom is still reactive toward polar organometallic compounds.

The literature on this subject describes attempts to introduce the amino group into phenylboronic acid by nitrating the boronic acid and reducing the nitro group introduced. This provides an isomer mixture which, depending on the reaction conditions, consists mainly of ortho- or of meta-nitrophenylboronic acid (in each case 60–70% yield); para-nitrophenylboronic acid could only be obtained as a by-product in very small amounts, but could not be fully characterized. Ortho- and meta-aminophenylboronic acids were prepared in moderate yields by reducing the nitro compounds, either with iron(II) salts or hydrogen over platinum, and isolated as the carboxanilides (Seaman and Johnson, J. Am. Chem. Soc. 1931, 53, 713). In the nitration, a certain fraction of nitrobenzene and boric acid was always obtained, even though operation was effected at low temperatures (down to −30° C., see below). In the subsequent publication (Bean and Johnson, J. Am. Chem. Soc. 1932, 54, 4415), this loss of the boron group was even described as an exclusive reaction in the nitration of 4-methoxyphenylboronic acid. Here too, later functionalization of phenylboronic acids in the para-position failed completely. The sensitivity of the boron-carbon bond in aromatics toward electrophiles was demonstrated by Kuivila and Hendrickson (J. Am. Chem. Soc. 1952, 74, 5068) by brominolysis of phenylboronic acids. It was found that electron-deficient phenylboronic acids were more stable than electron-rich phenylboronic acids, which was later utilized to synthesize some boronic acids having electron-withdrawing substituents (Torssell, Meyer, Zacharias, Ark. Kemi 1957, 10, 35, 497). The same publication also describes the preparation of a 4-amino-3-nitrophenylboronic acid in a multistage sequence starting from tolylboronic acid. In this synthesis, tolylboronic acid was nitrated at low temperature (−40° C.), the methyl group was oxidized to the acid, an azide was introduced via the acid chloride, the former was decomposed by Curtius reaction to give the acetylamino group and this was hydrolyzed (14% overall yield).

A further method of forming boronic acid derivatives is the transition metal-catalyzed coupling of dioxaborolanes (cf. Murata et al., J. Org. Chem. 2000, 65, 164) or dioxaborolanyls (cf. Zaidlewicz et al., J. Organomet. Chem. 2002, 657, 129) with haloaromatics. However, this reaction with haloanilines having a 7% yield has hitherto not proceeded satisfactorily (Baudoin et al., J. Org. Chem. 2000, 65, 9268).

In addition, the introduction of a boronic acid function into an aromatic nitro compound with subsequent hydrogenation would be conceivable; however, as a consequence of the reactivity of the nitro group, this requires extremely low temperatures and is restricted to few substrates (cf. Köbrich et al., Angew. Chem. 1966, 78, 1062; Knochel et al., Angew. Chem. 2002, 114, 1680).

It is therefore an object of the present invention to provide a process which allows anilineboronic acids (aminophenylboronic acids), in particular those which bear the amino group in the para-position, and their derivatives to be prepared and is compatible with many substituents and substitution patterns, comprises neither multistage synthetic sequences nor reactions such as the Curtius degradation which are industrially difficult to control, achieves high yields and is economically viable. This is the prerequisite for an industrial preparation and further usability of aminophenylboronic acids.

The present invention fulfils these demands and relates to a process for preparing optionally substituted anilineboronic acid derivatives of the formula (I) and derivatives thereof Step 1: Protection of the Aniline by Dibenzylation

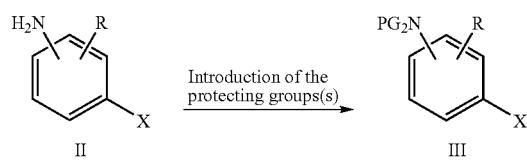

Step 2: Metalation of the Protected Aniline, Conversion to Boronic Acid Derivative

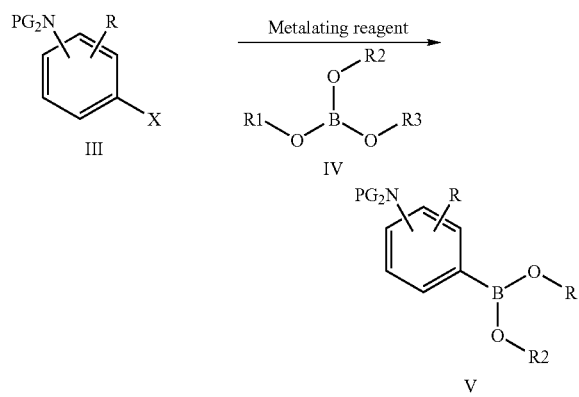

Step 3: Detachment of the Protecting Group

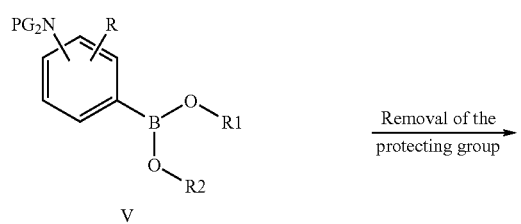

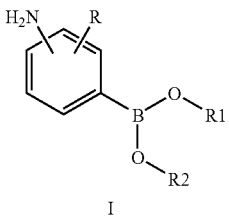

by converting an aniline (II) to a diprotected aniline (III) by introducing two protecting groups PG, metalating (III) and simultaneously or subsequently reacting with a boronic ester $B(OR^{1,2,3})_3$ (IV) to a protected aminophenylboronic ester of the formula (V), which is converted, by detaching the protecting groups PG, to the anilineboronic esters of the formula (I)

where

R is H, F, Cl, Br, I, a branched or unbranched, optionally substituted $C_1$–$C_{20}$—, in particular $C_1$–$C_8$-alkyl or -alkoxy radical, an optionally substituted $C_6$–$C_{12}$-aryl or -aryloxy radical, in particular phenyl, a heteroaryl or heteroaryloxy radical, an optionally substituted $C_3$–$C_8$-cycloalkyl radical, in particular cyclohexyl, a dialkyl or diarylamino group, an alkyl or arylthio group, or an ester or acetal group;

X is H, Cl, Br, I or F, in particular Cl or Br;

$R^1$, $R^2$, $R^3$ are each independently H, a branched or unbranched, optionally substituted $C_1$–$C_{20}$—, in particular $C_1$–$C_8$-alkyl group, and two $R^{1-3}$ radicals together may optionally form a ring, or are each further $B(OR)_3$ radicals.

PG represents a protecting group which is inert under the conditions of the metalation and borylation and can be removed from (V) without loss of the boron function, for example an optionally substituted benzyl, 2,4-dimethoxybenzyl, triorganosilyl, in particular trialkylsilyl, tert-butyloxycarbonyl, benzyloxycarbonyl, organosulfonyl or organocarbamoyl group, and two such protecting groups together may also form a ring, or represent a trimeric 1,3,5-trisaralhexahydro-1,3,5-triazine which can be described in a formal sense as the condensation product of three equivalents of the compound (II) with formaldehyde.

Protecting groups PG which can generally be used under the process conditions are known to those skilled in the art.

Introduction of the protecting group PG fully protects the hydrogen atoms attached to the nitrogen, so that the amine function can no longer be attacked in the subsequent metalation step.

The protecting groups PG can be introduced, for example, by alkylating the aniline nitrogen atom with an alkylating agent, optionally also using a base and/or a catalyst, or by reductively aminating an optionally substituted benzaldehyde with the aniline (II) with the aid of a hydride donor.

When the protecting groups PG used are carbamoyl or acyl groups, it has been found to be advantageous to introduce these by acylating the aniline nitrogen atom by means of reactive carboxylic acid derivatives; this may optionally be effected in the presence of an acylation catalyst or also using a base or an alkali metal.

Triorganosilyl groups as protecting groups are preferably introduced by reacting the aniline derivative with an electrophilic silylating agent; this is optionally effected also using a base or an alkali metal.

X is preferably chlorine, bromine or iodine, more preferably bromine in the case of metalation by halogen-metal exchange, more preferably chlorine in the case of lithiation with metallic lithium.

Useful metalating reagents include, for example, Grignard compounds, diorganomagnesium compounds, organolithium compounds or triorganomagnesium ate complexes, and also alkali metal diorganoamides, combinations of organolithium compound and complexing agent, combinations of organolithium compound and alkali metal alkoxide, or else the reactive metal itself such as alkali metals and alkaline earth metals, in particular sodium, lithium, magnesium or else zinc in a suitable form, optionally in the presence of a redox catalyst.

Metalation of (III) provides compounds of the formula (IIIa) where M is an alkali metal or alkaline earth metal optionally bearing ligands, or zinc, cadmium or mercury.

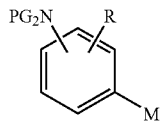

II

Particularly preferred metalating reagents are secondary Grignard compounds such as isopropyl-, cyclohexyl- or cyclopentylmagnesium halides, and primary or secondary alkyllithium compounds such as butyllithium, hexyllithium or cyclohexyllithium, or metallic lithium in in the presence of a catalyst.

The thus obtained metalated compound (IIIa) is reacted with from 0.6 to 5 equivalents, especially from 1 to 4 equivalents, of a triorganoborate of the formula

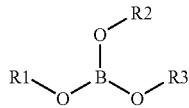

III to give compounds of the formula (V). The $R^{1-3}$ radicals are in this case each as defined above.

The $R^{1-3}$ radicals are preferably each alkyl radicals which belong in particular to the group of linear or branched lower alkanes and cycloalkanes, in particular methyl, ethyl, propyl, butyl, isopropyl, isobutyl, tert-butyl, pentyl, isopentyl, neopentyl, cyclopentyl, hexyl, isohexyl, cyclohexyl, cycloheptyl, cyclooctyl, etc.

Subsequent detachment of the protecting groups PG on the aniline nitrogen atom, for example by hydrolysis or in a subsequent reaction step, leads to the desired anilineboronic acid derivatives (I).

To remove the protecting group, any method can be used which is compatible with the other functions present in the molecule, for example hydrogenolysis or transfer hydrogenolysis in the case of benzyl groups or benzyloxycarbonyl groups, dilute acid in the case of silyl- or dimethoxybenzyl groups, fluoride in the case of silyl groups, etc. The hydrogenolysis is preferably effected in a hydrogenous atmosphere in the presence of a transition metal catalyst, under a pressure of from 0.5 to 400 bar, in particular from 2 to 200 bar.

A particularly preferred method for removing PG is the catalytic hydrogenation in the case of benzyl groups and benzyloxycarbonyl groups and the fluoride-induced desilylation in the case of silyl groups and the acidic cleavage in the case of dimethoxybenzyl groups and tert-butyloxycarbonyl groups.

Further methods for detaching PG are the transfer hydrogenation in the presence of a transition metal catalyst and of a suitable hydride donor or the reaction with a Brønsted or Lewis acid or Brønsted base.

The process according to the invention is carried out in a solvent, at temperatures in the range from −100 to 120° C., preferably in the range from 0 to 40° C. When Grignard compounds are used, the temperature is in particular in the preferred range; when organolithium compounds are used, preferably in the range from −100° C. to −30° C. in the metalation. As a consequence of the moisture and oxygen sensitivity of the organometallic reagents and intermediates, the reaction is preferably carried out under a dry inert gas such as nitrogen or argon.

The metalation step of the process according to the invention is carried out in an organic solvent or solvent mixture, preferably in an aliphatic, aromatic or ethereal solvent or mixtures of these solvents, more preferably in solvents or solvent mixtures which comprise at least one solvent selected from the following group: tetrahydrofuran, lower [lacuna], glyme, diglyme, toluene, cyclohexane, pentane, hexane, isohexane or heptane, triethylamine, dialkyl ethers, in particular diethyl ether, di-n-propyl ether, diisopropyl ether, dibutyl ether, 2-methyltetrahydrofuran, tert-butyl methyl ether, benzene, xylene, anisole, petroleum ether (alkane mixtures), methylcyclohexane.

Protection and deprotection step are carried out either in substance or a suitable solvent, for example from the group of the aforementioned solvents or solvent mixtures.

In the preferred embodiment, the aniline (II) is initially reacted with from 1 to 50 equivalents of a compound which transfers the protecting group PG, more preferably with from 2 to 2.2 equivalents, in a suitable solvent, usually in the presence of from 1 to 20 equivalents of a suitable base. The workup to isolate (II) is effected in a manner adapted to the sensitivity of the protecting groups.

In the preferred embodiment of the second step, a Grignard compound is initially charged at room temperature or an alkyllithium compound at low temperature, and the protected haloaniline (III) is slowly metered in and is metalated by halogen-metal exchange. Afterward, the resulting suspension is admixed with the triorganoboric ester and stirred to complete conversion, in the course of which the temperature is optionally increased. Equally, the compound (III) may be initially charged and the organometallic compound metered in.

In an alternative embodiment as a one-step variant, the triorganoboric ester $B(OR^{1-13})_3$, which in this case preferably bears sterically demanding substituents, is initially charged with the protected haloaniline (Ill) and the organometallic compound is metered in.

In a further alternative embodiment, a protected lithioaniline can be obtained by deprotonating an aniline (III), for which the base used is generally an alkyl- or aryllithium compound, a lithium amide (for example lithium diisopropylamide) or a combination of organolithium compound and complexing agent (for example butyllithium and N,N,N',N'-tetramethylethylenediamine) or a combination of organolithium compound and alkali metal alkoxide (for example butyllithium and potassium tert-butoxide). In this case too, it is possible either to initially charge the organometallic base or to initially charge the compound (III) or a mixture of compound (III) and $B(OR^{1-3})_3$.

In a further alternative embodiment, the protected haloaniline (III) is reacted with a reactive metal, in particular lithium or magnesium, optionally in the presence of a catalyst, in order to generate the reactive metalated species. This may then be reacted with the triorganoboric ester in one of the ways described. The direct metalation of (III) may also be effected in the presence of the boronic ester.

The workup is generally effected under the customary aqueous conditions, and (V) is obtained either as the boronic ester, boronic acid or boronic anhydride.

The detachment of the protecing groups, if not already effected during the workup of the boronic acid derivative, is carried out under precisely controlled conditions in a way which is compatible with the functionalities of (IV), especially the boronate group, i.e. leads to very little protodeboronation. Optionally, the resulting anilineboronic acid derivative (I) can be further purified by recrystallization, or be isolated as a salt, for example as the hydrochloride.

The thus obtained anilineboronic acid derivative, in particular aminophenylboronic acids, esters and anhydrides, can be used in Suzuki couplings without any problem. The process for the first time offers a simple, cost-effective route to the synthesis of these compounds in good yields.

One advantage of the process according to the invention is the good accessibility of anilineboronic acid derivatives of the formula (I), especially of 4-aminophenylboronic acid derivatives which are not accessible by the existing processes. A further advantage of the process according to the invention is that the introduction of the protecting groups usually does not require any expensive organometallic bases, for example lithium alkyls. A further advantage is that the diprotected amino group is inert with respect to the metalation of the aromatic rings in a wide temperature range, so that cryogenic conditions can frequently be dispensed with.

The process according to the invention is to be illustrated by the following examples, without the invention being restricted thereto:

EXAMPLE 1

4-Aminophenylboronic acid by halogen-metal exchange by means of hexyllithium on N,N-dibenzyl-4-bromoaniline A mixture of 17.2 g (100 mmol) of 4-bromoaniline, 35.9 g (210 mmol) of benzyl bromide and 16 g (151 mmol) of sodium carbonate in 100 ml of N,N-dimethylformamide was stirred at 100–110° C. for 10 h and the reaction mixture was poured into 400 ml of ice-water. The resultant precipitate was filtered off, washed with water and cold methanol, and dried under reduced pressure. Yield of 4-bromo-N,N-dibenzylaniline: 32.37 g (91.9 mmol, 92%)

A solution of 20.15 g (57.2 mmol) of 4-bromo-N,N-dibenzylaniline in 120 ml of tetrahydrofuran was cooled to −78° C., admixed slowly with 31 ml (62.9 mmol) of a 2.02 M solution of hexyllithium in hexane, stirred for a further 30 min and then admixed with 15.8 ml (68.6 mmol) of triisopropyl borate and stirred under cold conditions for a further 1 h. The reaction mixture was warmed to room temperature, concentrated and admixed with 150 ml of ethyl acetate and 57 ml of water. The organic phase was removed, dried over sodium sulfate and concentrated. The resulting solid was suspended in 50 ml of hexane, filtered off and washed with 75 ml of ethyl acetate. The filtrate was concentrated and the residue treated likewise. 13.05 g (14.54 mmol, 76%) of the cyclotrimeric anhydride of 4-(N,N-dibenzylamino)-phenylboronic acid were obtained as a colorless solid.

6.28 g (7.0 mml) of the trimeric 4-(N,N-dibenzylamino) phenylboronic anhydride and 126 mg of palladium on activated carbon (10%) were taken up in 50 ml of methanol in hydrochloric acid solution and stirred under hydrogen atomosphere (1–3 bar) for 3 h. The catalyst was filtered off and the filtrate concentrated. 3.45 g (19.9 mmol, 95%) of 4-aminophenylboronic acid hydrochloride were obtained as a light brown solid. Overall yield over three steps 66%.

EXAMPLE 2

3-Aminophenylboronic acid by halogen-metal exchange by means of hexyllithium on N,N-dibenzyl-3-bromoaniline 3-bromoaniline was protected, reacted and worked up as described in example 1 for 4-bromoaniline. 3-Aminophenylboronic acid was obtained in a 67% overall yield.

EXAMPLE 3

2-Aminophenylboronic acid by halogen-metal exchange by means of hexyllithium on N,N-dibenzyl-2-bromoaniline 2-Bromoaniline was protected, reacted and worked up as described in example 1 for 4-bromoaniline. 2-Aminophenylboronic acid was obtained in a 64% yield.

EXAMPLE 4

4-Aminophenylboronic acid by reaction of N,N-dibenzyl-4-bromoaniline with elemental lithium At −50° C., 655 mg (94.38 mmol) of lithium in 10 ml of tetrahydrofuran were admixed with 16.2 g (46.0 mmol) of N,N-dibenzyl-4-bromoaniline (preparation: see example 1) and a catalytic amount of biphenyl in 40 ml of tetrahydrofuran. The mixture was left to stir at this temperature for 19 h and the resulting reaction mixture was admixed slowly with cooling with 12.7 ml (55.2 mmol) of triisopropyl borate. The mixture was allowed to warm slowly to room temperature, methanol was added and the mixture was concentrated. The crude product was diluted with 150 ml of ethyl acetate and 50 ml of water. The organic phase was removed, dried over sodium sulfate and concentrated. After recrystallization of the residue from ethyl acetate, 10.94 g (12.19 mmol, 79%) of trimeric 4-(N,N-dibenzylamino)phenylboronic anhydride were obtained. The detachment of the protecting groups by hydrogenolysis was carried out as described in example 1. The yield was 97%, the overall yield 70.5%.

EXAMPLE 5

4-Aminophenylboronic acid by reaction of N,N-dibenzyl-4-chloroaniline with elemental lithium N,N-Dibenzyl-4-chloroaniline was prepared by benzylating 4-chloroaniline with benzyl bromide in a similar manner to N,N-dibenzyl-4-bromoaniline (see example 1); the yield was 97%.

A solution of 17.0 g (55.3 mmol) of N,N-dibenzyl-4-chloroaniline and a catalytic amount of biphenyl in 50 ml of tetrahydrofuran was added at −30° C. to a mixture of 786 mg (113 mmol) of lithium in 10 ml of tetrahydrofuran and stirred between −40 and −30° C. for 24 h. At −40° C., 14.0 ml (60.8 mmol) of triisopropyl borate were added and the mixture was allowed to warm slowly to room temperature. Some methanol was added and the mixture was concentrated. The residue was taken up in 150 ml of ethyl acetate and 60 ml of water. The organic phase was removed, dried over sodium sulfate and concentrated, and the residue was dissolved in 15 ml of ethyl acetate. In the course of 12–15 h, 10.65 g (11.84 mmol, 67%) of 4-(N,N-dibenzylamino)phenylboronic anhydride crystallized out.

The removal of the protecting groups by hydrogenolysis was carried out as described in example 1 (93%). The overall yield was 60%.

EXAMPLE 6

3-Amino-5-trifluoromethylphenylboronic acid by halogen-metal exchange by means of isopropylmagnesium bromide on 3-(N,N-dibenzylamino)-5-bromobenzotrifluoride 3-(N,N-Dibenzylamino)-5-bromobenzotrifluoride was prepared by benzylating 3-amino-5-bromobenzotrifluoride with benzyl bromide in a similar manner to N,N-dibenzyl-4-bromoaniline (see example 1); the yield was 88%.

6.86 g (16.3 mmol) of the resulting 3-(N,N-dibenzylamino)-5-bromobenzotrifluoride were dissolved in 20 ml of tetrahydrofuran, cooled to 0° C. and admixed slowly with 28 ml (19.6 mmol) of an approx. 0.7 M solution of isopropylmagnesium bromide in tetrahydrofuran. The mixture was allowed to warm gradually to room temperature and then stirred for another 2 h. The mixture was then cooled again to 0° C. and 5.1 ml (22.0 mmol) of triisopropyl borate were slowly added dropwise. The mixture was left to stir at room temperature overnight. For workup, some methanol was added to the reaction mixture which was concentrated. The crude product was taken up in 150 ml of ethyl acetate and 50 ml of semisaturated ammonium chloride solution, and the organic phase was removed, dried over sodium sulfate and concentrated. The residue was suspended in 50 ml of hexane and the product was filtered off, the filtrate was concentrated and the residue was once again suspended in a little hexane and filtered. Both product fractions together gave 1.73 g (3.33 mmol, 61%) of 3-amino-5-trifluoromethylphenylboronic anhydride.

The removal of the benzyl groups was carried out by hydrogenolysis as described in example 1 (89%). The overall yield was 48%.

EXAMPLE 7

4-Aminophenylboronic acid by Grignard reaction on N,N-bis(trimethylsilyl)-4-bromoaniline 10.0 g (58.1 mmol) of 4-bromoaniline were dissolved in 200 ml of triethylamine and admixed with 25 ml (130 mmol) of trimethylsilyl trifluoromethanesulfonate. The mixture was heated to reflux for 8 h. The reaction mixture was concentrated and the crude product distilled under high vacuum. 11.9 g (37.8 mmol, 65%) of N,N-bis(trimethylsilyl)-4-bromoaniline were obtained.

10.0 g (31.6 mmol) of N,N-bis(trimethylsilyl)-4-bromoaniline were metered gradually into a suspension of 0.99 g (41.1 mmol) of magnesium in 70 ml of tetrahydrofuran while it was boiled under reflux. Boiling under reflux was continued for another 10 h and the reaction mixture was cooled to 0° C. 9.4 ml (40.8 mmol) of triisopropyl borate were added to the solution of 4-N,N-bis(trimethylsily)aminophenylmagnesium bromide and the mixture was stirred at room temperature overnight. To detach the silyl groups, 65 ml (65 mmol) of a 1 M solution of tetrabutylammonium fluoride in tetrahydrofuran (5% water) was added and stirring was continued for 1 h.

For workup, the reaction mixture was added to 250 ml of water and 250 ml of ethyl acetate, and the organic phase was removed, dried over sodium sulfate and concentrated under reduced pressure. Repeated recrystallization from methanol in weak hydrochloric acid solution afforded 1.92 g (11.1 mmol, 35%) of 4-aminophenylboronic acid hydrochloride as a brown solid (yield over both stages 23%).

EXAMPLE 8

4-Amino-3-methylboronic acid by halogen-metal exchange on 4-(N,N-bis(trimethylsilyl)amino)-3-methylbromobenzene Starting from o-toluidine, the introduction of the silyl protecting groups was carried out in a similar manner to example 5. N,N-bis(trimethylsilyl)-4-bromo-3-methylaniline was obtained in a 57% yield.

15 g (30.3 mmol) of the substance, dissolved in 60 ml of tetrahydrofuran, were cooled to −78° C. and admixed slowly with 19 ml (30.3 mmol) of a 1.6 M solution of butyllithium in hexane. The mixture was left to stir for another 10 min and then a solution of 4.72 g of trimethyl borate (45.5 mmol) in 20 ml of tetrahydrofuran was added dropwise at not more than −50° C. The mixture was left to stir at this temperature for another hour and then warm to room temperature overnight. The mixture was hydrolyzed with 40 ml of saturated potassium fluoride solution and admixed with 100 ml of toluene, and the phases were separated. The organic phase was concentrated. The residue was purified by recrystallization to obtain 2.34 g (5.3 mmol, 51%) of trimeric 4-amino-3-methylboronic anhydride as a slightly brownish solid (yield over both stages 29%).

EXAMPLE 9

4-Aminophenylboronic acid by halogen-metal exchange by means of isopropylmagnesium bromide on N,N-bis(tert-butyloxycarbonyl)-4-iodoaniline 5 g (15.7 mmol) of N-tert-butyloxycarbonyl-4-iodoaniline (BOC-protected 4-iodoaniline) in 30 ml of toluene were admixed at room temperature with a spatula-tip of 4-dimethylaminopyridine as a catalyst and 5.02 g (23.0 mmol) of di-tert-butyl dicarbonate (BOC anhydride). The mixture was left to stir overnight, diluted with 30 ml of dichloromethane and washed with 20 ml of 5% hydrochloric acid, the phases were separated and the organic phase was concentrated to dryness. The residue was freed of solvent residues in high vacuum. BOC-diprotected 4-iodoaniline was obtained in a 4.41 g (10.5 mmol, 67%) yield.

The entire amount was dissolved in 25 ml of THF and added dropwise to a solution, cooled to −78° C., of lithium tributylmagnesate in THF/hexane (approx. 44 ml, 12.6 mmol) (prepared from butylmagnesium bromide solution in THF and butyllithium solution in hexane at 0 C). After stirring for a further 40 min, 3.27 g (31.5 mmol) of trimethyl borate were slowly added dropwise. The mixture was stirred at −78° C. for another 30 min and then allowed to warm slowly to 0° C. For hydrolysis, 70 ml of 2 N methanolic hydrogen chloride were added and the mixture was stirred for 7 h. To isolate the product, the mixture was added to 250 ml of water and 250 ml of toluene, extraction was effected and the phases were separated. The toluene phase was concentrated and the product recrystallized from methanol. 0.64 g (3.7 mmol, 35%) of 4-anilineboronic acid hydrochloride was obtained; additionally, an undetermined amount of aniline had formed by protodeboronation (yield over both stages 23.5%).

EXAMPLE 10

2-Aminophenylboronic acid by direct ortho-metalation by means of hexyllithium on N,N-dibenzylaniline A solution of 10.0 g (36.58 mmol) of commercially available N,N-dibenzylaniline and 5.5 ml (36.6 mmol) of N,N,N',N'-tetramethylethylenediamine in 100 ml of tetrahydrofuran was cooled to −78° C., admixed slowly with 18.1 ml (36.6 mmol) of a 2.02 M solution of hexyllithium in hexane, stirred at −50° C. for 4 h and then admixed at −78° C. with 9.3 ml (40 mmol) of triisopropyl borate and stirred under cold conditions for another 1 h. The reaction mixture was warmed to room temperature, concentrated and admixed with 100 ml of ethyl acetate and 40 ml of water. The organic phase was removed, dried over sodium sulfate and concentrated under reduced pressure. The resulting residue was suspended in 30 ml of hexane, filtered off and washed with a little cold ethyl acetate. The filtrate was concentrated and the residue treated likewise. 9.41 g (10.49 mmol, 86%) of the cyclotrimeric anhydride of 4-(N,N-dibenzylamino)phenylboronic acid were obtained as a colorless solid.

The hydrogenolysis of example 1 gave a yield of 92% (overall yield over both stages 79%).

What is claimed is:

1. A process for preparing an anilineboronic acid derivative of the formula I

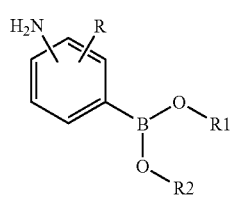

comprising the steps of:
step 1: converting an aniline (II) to a diprotected aniline (III) by introducing two protecting groups PG,
step 2: metalating the diprotected aniline (III) with a metalating agent and simultaneously or subsequently reacting with a boronic ester $B(OR^{1,2,3})_3$ (IV) to a protected anilineboronic ester of the formula (V), and
step 3: detaching the protecting groups PG, to form the anilineboronic ester of the formula (I)

Step 1: Protection of the aniline by dibenzylation

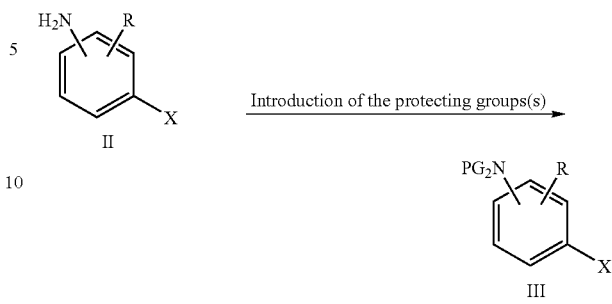

Step 2: Metalation of the protected aniline, conversion to boronic acid derivative

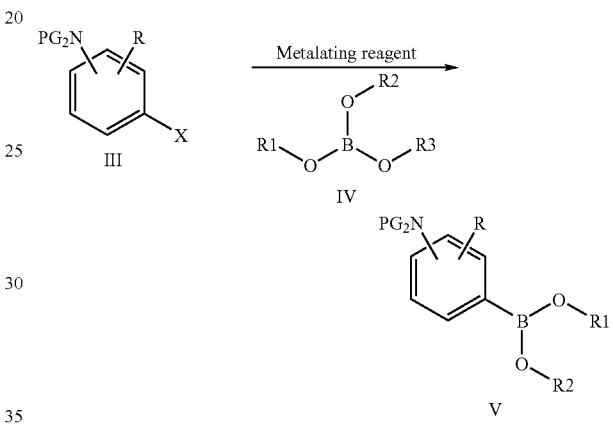

Step 3: Detachment of the protecting group

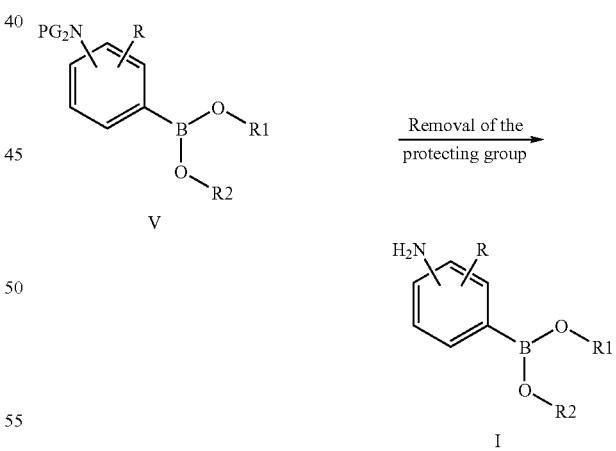

where
R is H, F, Cl, Br, I, a branched or unbranched, substituted or unsubstituted $C_1$–$C_{20}$—, a substituted or unsubstituted $C_6$–$C_{12}$-aryl or -aryloxy radical, a heteroaryl radical, a heteroaryloxy radical, a substituted or unsubstituted $C_3$–$C_8$-cycloalkyl radical, a dialkyl group, a diarylamino group, an alkyl group, an arylthio group, an ester group or acetal group;
X is H, Cl, Br, I or F;

$R^1$, $R^2$, $R^3$ are each independently H, a branched or unbranched, substituted or unsubstituted $C_1$–$C_{20}$-alkyl group, and two $R^{1-3}$ radicals together may optionally form a ring, or are each further $B(OR^{1,2,3})_3$ radicals.

2. The process as claimed in claim 1, wherein the protecting groups PG are substituted or unsubstituted benzyl groups and step 1 further comprises alkylating the aniline (II) nitrogen atom with an alkylating agent.

3. The process as claimed in claim 1, wherein the protecting groups PG are substituted or unsubstituted benzyl groups and wherein step 1 further comprises reductively aminating a substituted or unsubstituted benzaldehyde with the aniline (II) in the presence of a hydride donor.

4. The process as claimed in claim 1, wherein the protecting groups PG are carbamoyl or acyl groups bearing organic substituted or unsubstituted radicals and wherein step 1 further comprises acylating the aniline (II) nitrogen atom with at least one reactive carboxylic acid derivative.

5. The process as claimed in claim 1, wherein the protecting groups are triorganosilyl groups and wherein step 1 further comprises reacting the aniline (II) with an electrophilic silylating agent.

6. The process as claimed In claim 1, wherein step 3 further comprises hydrogenolysis in a hydrogenous atmosphere in the presence of a transition metal catalyst under a pressure of from 0.5 to 400 bar.

7. The process as claimed in claim 1, wherein step 3 further comprises transfer hydrogenation in the presence of a transition metal catalyst and one of a hydride donor, a Brønsted or Lewis acid or Brønsted base.

8. The process as claimed in claim 1, wherein step 2 further comprises reading the diprotected aniline (III) with an organomagnesium or organolithium compound.

9. The process as claimed in claim 1, wherein step 2 further comprises reacting the diprotected aniline (III) with a reactive metal selected from the group consisting of: alkali metals, alkaline earth metals and zinc.

10. The process as claimed in claim 1, wherein step 2 is carried out in at least one solvent selected from the group consisting of: triethylamine, diethyl ether, di-n-propyl ether, diisopropyl ether, dibutyl ether, tetrahydrofuran, 2-methyltetrahydrofuran, tert-butyl methyl ether, benzene, toluene, xylene, anisole, pentane, hexane, isohexane, heptane, petroleum ether (alkane mixtures), cyclohexane, and methylcyclohexane.

11. The process as claimed in claim 1, wherein step 2 further comprises initially charging the metalating agent in a solvent, and subsequently metering in the diprotected aniline (III) into the metalating agent and solvent to form a reaction mixture, and subsequently reacting the boronic ester $B(OR^{1,2,3})_3$ (IV) with the reaction mixture.

12. The process as claimed in claim 1, wherein step 2 further comprises initially charging the metalating agent in a solvent and the diprotected aniline (III) and the boronic ester $B(OR^{1,2,3})_3$ (IV) are metered in to the metalating agent and solvent in parallel or as a mixture.

13. The process as claimed in claim 1, wherein step 2 further comprises initially charging the diprotected aniline (III) in a first solvent and then the metalating agent and a second solvent is metered in to the diprotected aniline (III) and first solvent to form a reaction mixture, and reacting the boronic ester $B(OR^{1,2,3})_3$ (IV) with the reaction mixture.

14. The process as claimed in claim 1, wherein step 2 further comprises initially charging the diprotected aniline (III) and the boronic ester $B(OR^{1,2,3})_3$ in a solvent to form a reaction mixture (IV) and metering in the metalating agent into the reaction mixture.

15. The process as claimed in claim 1, wherein step 2 further comprises reacting the diprotected aniline (III) with a reactive metal in a solvent.

16. The process as claimed in claim 1, wherein step 2 further comprises reacting the diprotected aniline (III) and the boronic ester $B(OR^{1,2,3})_3$ (IV) with a reactive metal selected from the group consisting of: alkali metals, alkaline earth metals, and zinc.

17. The process as claimed in claim 1 carried out at a temperature in the range from −100 to 120° C.

18. The process as claimed in claim 1, wherein the metalating agent is a Grignard compound and step 2 is carried out in the range from 0 to 40° C.

19. The process as claimed in claim 2, wherein step 1 further comprises alkylating the aniline nitrogen atom with an alkylating agent and at least one of a base or a catalyst.

20. The process as claimed in claim 4, wherein step 1 further comprises acylating the aniline (II) nitrogen atom with at least one reactive carboxylic acid derivative in the presence of at least one of acylation catalyst, base or alkali metal.

21. The process as claimed in claim 5, wherein step 1 further comprises reacting the aniline (II) with an electrophilic silylating agent in the presence of a base or an alkali derivative.

22. The process as claimed in claim 9, wherein step 2 further comprises using a redox catalyst.

23. The process as claimed in claim 15, wherein step 2 further comprises using a redox catalyst.

24. The process as claimed in claim 16, wherein step further comprises using a redox catalyst.

25. The process as claimed in claim 11, wherein the boronic ester $B(OR^{1,2,3})_3$ (IV) is mixed with a solvent prior to reaction with the reaction mixture.

26. The process as claimed in claim 1, wherein the metalating agent is an organolithium compound and step 2 is carried out at a temperature in the range from −100° C. to 30° C.

* * * * *